United States Patent
Herrmann et al.

(10) Patent No.: US 9,980,894 B2
(45) Date of Patent: May 29, 2018

(54) COSMETIC COMPOSITIONS COMPRISING HYALURONAN BIOSYNTHESIS PROMOTING AGENTS

(75) Inventors: Martina Herrmann, Hameln (DE); Gerhardd Schmaus, Höxter (DE)

(73) Assignee: Symrise AG, Holzminden (DE)

( * ) Notice: Subject to any disclaimer, the term of this patent is extended or adjusted under 35 U.S.C. 154(b) by 505 days.

(21) Appl. No.: 14/408,117

(22) PCT Filed: Jun. 15, 2012

(86) PCT No.: PCT/EP2012/061490
§ 371 (c)(1),
(2), (4) Date: Mar. 10, 2015

(87) PCT Pub. No.: WO2013/185843
PCT Pub. Date: Dec. 19, 2013

(65) Prior Publication Data
US 2015/0174033 A1    Jun. 25, 2015

(51) Int. Cl.
| | |
|---|---|
| *A61K 8/02* | (2006.01) |
| *A61K 8/49* | (2006.01) |
| *A61K 8/35* | (2006.01) |
| *A61Q 11/00* | (2006.01) |
| *A61Q 19/00* | (2006.01) |
| *A61Q 19/08* | (2006.01) |
| *A61Q 5/00* | (2006.01) |

(52) U.S. Cl.
CPC ............. *A61K 8/4973* (2013.01); *A61K 8/35* (2013.01); *A61Q 5/00* (2013.01); *A61Q 11/00* (2013.01); *A61Q 19/00* (2013.01); *A61Q 19/007* (2013.01); *A61Q 19/08* (2013.01)

(58) Field of Classification Search
CPC .......... A61K 8/817; A61K 8/86; A61K 8/897; A61K 8/899; A61K 9/06; A61K 9/10; A61K 9/1075; A61K 2800/51; A61Q 13/00; A61Q 19/00; A61Q 19/10; A61Q 15/00; A61Q 5/02; A61Q 17/04; A61Q 5/00; A61Q 1/02; A61Q 1/06
See application file for complete search history.

(56) References Cited

U.S. PATENT DOCUMENTS 6,090,774 A * 7/2000 Moscona .................. A61K 8/02
                                                    510/101
2006/0165622 A1* 7/2006 Hiramoto ............... A61K 8/347
                                                    424/65

FOREIGN PATENT DOCUMENTS

| DE | 10 2006 050984 A1 | 4/2008 |
|---|---|---|
| DE | 10 2009 055915 A1 | 6/2011 |
| DE | 10 2009 055918 A1 | 6/2011 |
| DE | 10 2009 055919 A1 | 6/2011 |
| DE | 10 2009 055920 A1 | 6/2011 |
| EP | 1 800 651 A1 | 6/2007 |
| EP | 2 090 287 A2 | 8/2009 |
| EP | 2 090 301 A1 | 8/2009 |
| EP | 2 950 806 A1 | 4/2011 |
| EP | 2 327 393 A2 | 6/2011 |
| FR | 2 951 079 A1 | 4/2011 |
| FR | 2 962 333 A1 | 1/2012 |
| JP | 2002-029957 A | 1/2002 |
| WO | 2010/000877 A2 | 1/2010 |

* cited by examiner

*Primary Examiner* — Nannette Holloman
(74) *Attorney, Agent, or Firm* — Dilworth & Barrese, LLP

(57) ABSTRACT

Suggested is a cosmetic composition, comprising compounds of formula (I) wherein R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes formula (II) with X, Y and Z being independently of one another hydrogen, hydroxyl, an linear or branched $C_1$-$C_4$-alkyl group, or a linear or branched $OC_1$-$C_4$-alkyl group.

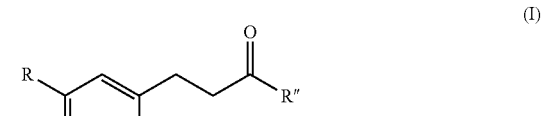

(I)

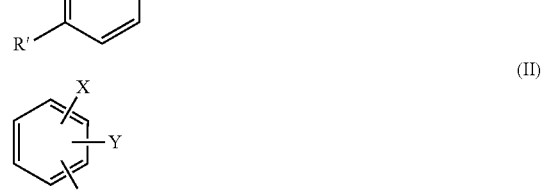

(II)

8 Claims, No Drawings

COSMETIC COMPOSITIONS COMPRISING HYALURONAN BIOSYNTHESIS PROMOTING AGENTS

FIELD OF INVENTION

The present invention belongs to the area of cosmetics and refers to a new group of hyaluronan biosynthesis promoting agents.

STATE OF THE ART

Hyaluronan (HA, hyaluronic acid) is an anionic, non-sulfated glycosaminoglycan (GAG) distributed widely throughout connective, epithelial and neural tissues. It is composed of repeating alternating units of glucuronic acid and N-acetyl-glucosamine. The molecular weight of HA ranges from $10^5$ to $10^7$ kDa. HA exists freely in extracellular spaces, but is also protein and cell-associated, resulting in the formation of pericellular coats. In solution at physiologic pH and salt concentration, HA is an expanded random coil with a mean diameter of 500 nm. The molecular domain encompasses a large volume of water.

HA is a major component of the extracellular matrix (ECM), particularly prominent in tissues undergoing rapid growth and development, during repair, and regeneration. Through its large hydrodynamic domain, hyaluronan helps to form a soft matrix, thus facilitating cell detachment, migration, and proliferation. In addition to these physico-chemical effects, hyaluronan induces intracellular signals through binding to cell surface receptors, such as CD44 (cluster of differentiation 44) and RHAMM (receptor for HA-mediated motility), thereby contributing to cellular processes like proliferation and migration.

HA as a space-filling material and organizer of an extensive extracellular matrix is a straightforward concept in mesenchymal/mesenchyme-derived tissues such as the dermis and cartilage. The vital parts of stratified epithelia in skin and of the oral, esophageal, and vaginal mucosa all exhibit an intense pericellular signal when stained with a hyaluronan-specific probe.

HA in skin occurs in both dermis and epidermis. The HA content of the dermis is far greater than that of the epidermis and accounts for most of the 50% of total HA present in skin. The papillary dermis has more prominent levels of HA than the reticular dermis. Dermal fibroblasts provide the synthetic machinery for dermal HA.

HA in the epidermis is strongly expressed around the basal and spinous cells, whereas the terminally differentiated cells of stratum corneum usually lack HA (R. Stern and H. I. Maibach., Clin Dermatol. 2008, 26(2), 106-122; R. Tammi et al., J. Invest. Dermatol. 2005, 124(5), 898-905).

The large volume that HA occupies including its cloud of solvent, the water of hydration under physiological conditions, underlies its ability to distend and maintain the extracellular space and preserve tissue hydration. The HA-bound water in the dermis and in the vital area of the epidermis is critical for skin hydration. The stratum granulosum, however, is essential for maintenance of said hydration, not only in skin, but also of the body in general. Profound dehydration is a serious clinical problem in patients with burns with extensive losses of stratum granulosum.

Another task of hyaluronan is maintenance of some extracellular space between the lower cells in the stratified structure of the epidermis to facilitate diffusion of nutritional supplies to and waste products from the upper cells.

HA is synthesized by action of HA synthases (HAS-1, -2 and -3) and catabolized primarily through hyaluronidases (HYAL).

The mechanism of ageing is generally divided into two different parts. The first is called intrinsic ageing caused by factors derived from within the body. The second part is classified as extrinsic ageing provoked by environmental factors. During the process of ageing several impairments can be observed, e.g. a decline in metabolic activity, a lower rate of cell division, a reduced DNA repair capacity, stiffening of vessel walls and an impaired peripheral blood circulation. All these aspects are closely linked to each other.

As skin ages, the amount and quality of HA in the skin is reduced. These changes lead to drying and wrinkling of the skin. The most dramatic histochemical change in cutaneous HA observed in senescent skin is the marked decrease in epidermal HA. In senile skin, HA is still present in the dermis, whereas HA of the epidermis has disappeared entirely. The proportion of total GAG synthesis devoted to HA is greater in the epidermis than in the dermis, and the reason for the age-related epidermal HA decrease is unknown. The synthesis of epidermal HA is influenced by the underlying dermis as well as by topical treatment, such as with retinoic acid or retinol which are known stimulators of the HA synthesis in epidermal keratinocytes, indicating that epidermal HA is under separate controls from dermal HA.

UVB irradiation is a key factor during extrinsic skin aging and it alters cutaneous structure and function. Repeated exposure to UV radiation from the sun causes premature aging of skin. Under conditions of increased formation of oxidative stress as associated e.g. with UV irradiation, HA can be significantly degraded by free radicals. Furthermore, collagen fragments in the dermis resulting from UVB-induced collagen degradation were shown to cause loss of the pericellular HA matrix and strongly reduced HA secretion in human skin fibroblasts through down-regulation of the predominant HAS isoform of fibroblasts HAS-2 (K. Röck et al., J. Biol. Chem. 2011, 286(20), 18268-18276).

HA is a hygroscopic macromolecule and its solutions are highly osmotic. In the oral mucosa, this property enables to control of tissue hydration during periods of inflammatory process or response to tissue injury resulting in ulcer formation. High-molecular-weight HA has been shown to be beneficial in supporting gingival health. It is the most abundant high-molecular-weight glycosaminoglycan (GAG) in the extracellular matrix of soft periodontal tissues. Studies indicate that HA exhibits beneficial activity in the treatment of gingivitis and periodontitis. Topically, HA has been used as a 0.2% solution for the treatment of recurrent aphthous ulcers in clinical trials (P. Kapoor et al., Indian J. Dermatol. 2011, 56(3), 300-302). HA application has also been proven to be beneficial in a number of medical disciplines.

Thus local, topical application of hyaluronan gel in conjunction with periodontal surgery resulted in a significant improvement of clinical attachment level and in a reduction in gingival recession versus placebo in a randomized controlled study (Fawzy El-Sayed K. M. et al., Clin. Oral Investig. 2011 Oct. 20, Epub ahead of print, DOI: 10.1007/s00784-011-0630-z). Promotors of endogenous HA synthesis should therefore also be beneficial in oral care products.

There exist cosmetic, dermatological or pharmaceutical (therapeutic) methods to apply exogenous HA. Traditionally extracted from rooster combs, exogenous HA is now mainly produced via microbial fermentation. It is used for the treatment of wrinkles, fine lines, and scars and is either injected as filler or topically applied. HA injections temporarily smooth wrinkles by adding volume under the skin, with effects typically lasting for six months.

In the past, surgical techniques have dominated the facial rejuvenation field. Volume restoration by injecting fillers has in many cases taken precedence over the two-dimensional lifting obtained when using the scalpel. Tissue volume augmentation via non-invasive procedures using soft tissue biodegradable fillers can restore the youthful appearance to an aging face. HA dermal fillers are the most popular, non-permanent injectable materials available to physicians today. However, injection of dermal fillers might result in undesirable adverse events and also HA-based dermal fillers are not devoid of inducing complications. The most common localized side effects, which usually resolve after a few days; encountered after treatments with HA dermal fillers are temporary pain, induration, bruising, tenderness, itching, edema, and erythema at the injection site. There have also been reports of hypersensitivity reactions ranging from 0.0005% to 0.42% and, in rare cases necrosis or embolisation might occur (F. S. Brandt and A. Cazzaniga, Clin. Interv. Aging 2008, 3(1), 153-159).

Many consumers however avoid and fear such invasive and also cost intensive treatment and prefer to achieve wrinkle reduction on a more long-term basis alternatively by using cosmetic products which can be applied topically.

HA and HA derivatives or salts can also be used topically incorporated in cosmetic, dermatological or pharmaceutical (therapeutic) formulations. Thus, topical application of 0.1% HA of formulations led to a significant improvement in skin hydration and elasticity (T. Pavicic et al., J. Drugs Dermatol. 2011, 10(9), 990-1000).

Also dry, scaly skin (xerosis) such as e.g. caused by atopic dermatitis (eczema) may be treated with a skin lotion e.g. marketed under the trade name Hylira gel, containing sodium hyaluronate as its active ingredient.

Due to an influence on signalling pathways, HA is also involved in the wound-healing process and scarless fetal healing. In clinical trials, topical application of HA improved wound healing; in particular, acute radioepithelitis, venous leg ulcers or diabetic foot lesions responded to HA treatment.

However, the addition of exogenous HA often does not recapitulate the effects of endogenous HA synthesis and topical high molecular weight HA is scarcely absorbed through the skin. For this reason, there has been a desire for the development of agents capable of promoting the biological HA synthesis of cells per se while making use of the self recuperative power which is innate in the living body, instead of externally supplementing HA.

Retinoids like retinoic acid, retinol, retinaldehyde and retinyl derivatives such as for example retinyl acetate, retinyl palmitate, retinyl retinoate are known to increase epidermal HA biosynthesis in keratinocytes (I. A. King, Br. J. Dermatol. 1984, 110(5), 607) and are thus often used as anti-ageing ingredients in skin care products. However, topical retinoids can cause severe skin reactions, including scaling, erythema, papules, and inflammation. In contrast to the HA promoting activity in the epidermis, retinoids inhibit the HA production in dermal fibroblasts (T. J. Smith, J. Clin. Endocrinol. Meatb. 1990, 70(3), 655-660).

Alpha-hydroxy acids such lactic acid, citric acid, and glycolic acid stimulate the HA biosynthesis in dermal fibroblasts. However, Individuals with sensitive skin may not tolerate some products formulated with alpha hydroxy acids (AHAs) due to unacceptable levels of stinging and irritation.

Transforming growth factor (TGF)-beta1 is known to increase HA synthesis in dermal fibroblasts but to down-regulate HA synthases in keratinocytes (S. Pasonen-Seppänen et al., J. Invest. Dermatol. 2003, 120(6), 1038-1044). But the cost of such growth factor makes its use as anti-ageing active almost impossible.

Furthermore several plant extracts and natural ingredients were shown to upregulate HA biosynthesis in skin cells. Thus for example *Articum lappa* fruit extract increased HAS-2 expression and HA level in human skin in an in vivo study (A. Knott et al., J. Cosmet. Dermatol. 2008, 7(4), 281-289) and an isoflavone and saponin containing soy extract enhanced the HA level in skin (K. M. Südel et al., Photochem. Photobiol., 2005, 81, 581-587). However plant extracts are often colored or lead to discoloration.

In the cosmetic, dermatological and pharmaceutical (therapeutic) industry, therefore, there is a constant need for hyaluronan biosynthesis promoting agents.

In this context reference is made to FR 2951079 A1 which relates to a fluid composition intended for protecting the skin and/or hair against ultraviolet radiation characterized by the fact that it comprises, in a cosmetically acceptable aqueous support, at least: (a) one photoprotective system capable of screening out UV radiation; and (b) one 2-alkoxy-4-alkyl ketone phenol compound e.g. [6]-paradol and gingerone (formula III). The concentration given for the 2-alkoxy-4-alkyl ketone phenol compound in the composition is preferably 0.01 to 10% by weight based on the total weight of the composition.

FR 2950804 A1 and FR 2950806 A1 disclose cosmetic, pharmaceutical or dermatological composition using at least one methoxyphenol derivative e.g. [6]-paradol and gingerone (formula III) as preservation system. The given quantity of the methoxyphenol derivative is higher than, or equal to 1% by weight based on the total weight of the composition.

WO 2010 062581 A1 relates to a skin augmentation composition comprising a therapeutically effective amount of a combination of a gingerol and a curcumin and a cosmetically or pharmaceutically acceptable carrier for enhancing the repair of damaged skin. [6]-Paradol is cited amongst other impurities that can be contained with the 6-gingerol component.

WO 2010 000877 A1 discloses formulation with synergistic irritation reducing action comprising bisabolol and [6]-paradol.

And finally DE 10 2006 050984 A1 relates to cosmetic composition containing amongst others 0.0001-5% of a substance producing a feeling of heat e.g. paradol. However, no feeling of heat can be perceived from [6]-paradol containing cosmetic formulations at concentrations which we found to be effective to stimulate the hyaluronan biosynthesis.

Therefore, object of the present invention was to provide effective agents stimulating the biological HA synthesis, preferably of a human skin cell and/or a human mucosal cell and thereby provide moisturizing and/or anti-ageing and/or wound healing promoting activity. The agents to be specified should be toxicologically safe, effective already at relatively low concentrations, well tolerated by the skin, stable (in particular in normal cosmetic and/or pharmaceutical formulations), colour- and odourless, not discolouring, easy to formulate and economical to produce.

DESCRIPTION OF THE INVENTION

Object of the present invention is a cosmetic composition comprising at least one active compound of formula (I)

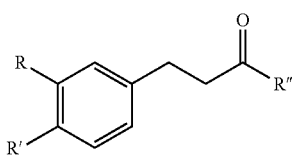

wherein
R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes

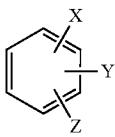

with X, Y and Z being independently of one another hydrogen, hydroxyl, an linear or branched $C_1$-$C_4$-alkyl group, or a linear or branched $OC_1$-$C_4$-alkyl group.

Surprisingly it has been found that compounds of formula (I) show pronounced HA biosynthesis promoting activity in human skin cells and this at astonishingly low concentrations and fulfil the complex profile explained above in all details.

Hyaluronan Stimulators

As set out above the compounds of formula (I) all represent suitable hyaluronan stimulators. The preferred types, however, follow one of formulae (II) to (V):

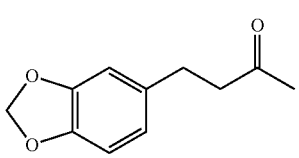

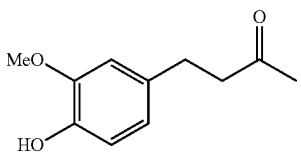

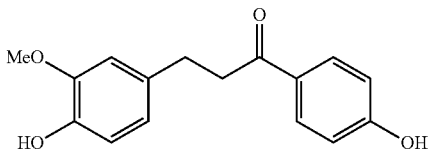

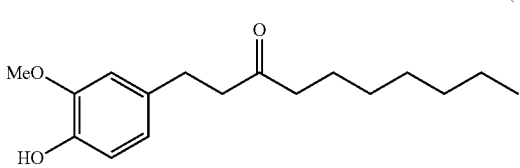

(i) 4-(3,4-methylendioxyphenyl)-2-butanone (formula II) also known as cassione, piperonyl acetone or dulcinyl potently enhance the in vitro HA biosynthesis in both epidermal keratinocytes and dermal fibroblasts. Piperonyl acetone is a known flavour and fragrance raw material with a sweet, floral, berry-like smell which also occurs naturally for example in the essential oil of *Ruta angustifolia*. As its odor strength is only medium, concentrations of >0.01% are used in finished cosmetic formulations and up to 15% in fragrance concentrates. JP 2002 029957 A1 describes skin lightening activity of piperonylmethylketone derivatives amongst them piperonyl acetone. In vitro efficacy on B16 melanoma cell line is observed between 520 µM (100 µg/ml) giving 87% inhibition and 26 µM (5 µg/ml) giving 15% inhibition and a cosmetic composition (preparation) preferably contains a total amount of 0.01 to 5.0% by weight, more preferably 0.05 to 3.0% by weight of piperonyl acetone based on the total weight of the composition.

(ii) 4-(4-hydroxy-3-methoxyphenyl)-2-butanone (formula III) also known as zingerone, gingerone, zingiberone, vanillylacetone or [0]-paradol also increases HA biosynthesis in both cells in vitro but with a more pronounced effect on epidermal keratinocytes. Zingerone is one of the pungent components of ginger extracts. In fresh ginger it is not or only in very limited concentrations present, but it is formed under disadvantageous conditions or during cooking from gingerols by a Retro-Aldol-reaction. It is used as a flavor additive in spice oils and in perfumery to introduce spicy aromas. For example, EP 2327393 A1 describes the use of zingerone in cosmetic and dermatologic preparations for the treatment and prevention of skin aging with a preferred dosage of 0.001-10%, more preferably 0.05-5% by weight based on the total weight of the preparation. The substance is described to act via stimulation of the differentiation of preadipocytes to adipocytes and thereby promoting the triglyceride (lipid) accumulation. Zingerone is also known for its anti-mutagenic and anti-carcinogenic activities that are often associated with its anti-oxidative and anti-inflammatory properties. DE 2009 10055915 A1 describes the use of zingerone for the preparation of cosmetic or dermatological compositions, which cause prickling or tingling sensation on the skin. The preferred dosage is 0.001-10%, more preferably 0.05-5% by weight based on the total weight of the composition.

(iii) 3-(4-Hydroxy-3-methoxyphenyl)-1-(4-hydroxyphenyl)-1-propanone (formula IV) powerfully upregulates HA synthesis in vitro in epidermal keratinocytes but has no direct stimulating effect on dermal fibroblasts. The active is known as anti-inflammatory (EP 2090301 A1), anti-oxidant (EP 2173697 A1) and anti-microbial (EP 2170796 A1) agent. The concentration of compound of formula IV given in these patent applications in cosmetic and pharmaceutical preparations is ranging from 0.001 to 20% by weight in relation to the total weight of the cosmetic or pharmaceutical preparation.

(iv) Finally, Heptyl 4-hydroxy-3-methoxyphenethyl ketone (formula V) also known as [6]-paradol or [6]-gingerone potently stimulates the in vitro HA biosynthesis of dermal fibroblasts but without any direct stimulating effect on epidermal keratinocytes. [6]-paradol is a pungent compound which naturally occurs for example in Guinea ginger (*Aframomum melegueta*) which is a plant used as a spice under the name "maniguette" or "grain of paradise" and to limited amounts also in ginger (*Zingiber officinale*). The compound is known for its anti-inflammatory, anti-oxidant and antitumor promoting activities. EP 1800651 A1 discloses anti-wrinkle and lipolysis promoting activity of 6-paradol. The given concentration of 6-paradol in external compositions for skin as an anti-wrinkle agent is preferably 0.001 to 10% by weight based on the total weight of the composition. If the formulated amount is less than 0.001%, the desired effects are inadequate according to EP 1800651 A1.

Preferred compounds of formula (I) are those in which R and R' do not denote hydroxyl at the same time. Further preferred compounds of formula (I) are those in which R and R' denote independently of one another hydrogen, hydroxyl, an $OC_1$-$C_2$-alkyl group, or optionally R and R' form together a methylenedioxy group resulting in a 3,4-methylendioxyphenyl residue with the exception of R=R'=hydroxyl. Even more preferred compounds of formula (I) are those in which R and R' denote independently of one another hydrogen, hydroxyl, an $OC_1$-$C_2$-alkyl group, or optionally R and R' form together a methylenedioxy group resulting in a 3,4-methylendioxyphenyl residue with the exception of R=R'=hydroxyl and R" denotes a linear or branched $C_1$-$C_9$ alkyl group or A with X, Y and Z of A being independently of one another hydrogen, hydroxyl, a $C_1$-C2-alkyl group, a $OC_1$-C2-alkyl group with the exception of X=Y=Z=hydroxyl.

Most preferred compounds of formula (I) are those which R and R' denote independently of one another hydrogen, hydrogen, a $OCH_3$ group, or optionally R and R' form together a methylenedioxy group resulting in a 3,4-methylendioxyphenyl residue with the exception of R=R'=hydroxyl and R" denotes a linear or branched $C_1$-$C_9$ alkyl group or A with X, Y and Z of A being independently of one another hydrogen, hydroxyl, $OCH_3$ with the exception of X=Y=Z=hydroxyl. The particularly preferred compounds of formula (I) are those of formula (II)-(V).

Compounds of formula (I) used according to the invention can either be synthetic or in case of natural occurrence also be used in the form of extracts or extract fractions from plants.

The cosmetic compositions, preferably topical cosmetic composition, according to the present invention preferably contains one or more compounds of formula (I) in a total amount of 0.000005-5% by weight, more preferably 0.000001-1% by weight, most preferably 0.00001-0.1% by weight, in each case based on the total weight of the composition.

Pharmaceutical and Dermatological Application

Another object of the present invention refers to a pharmaceutical or dermatological composition, comprising at least one active compound of formula (I)

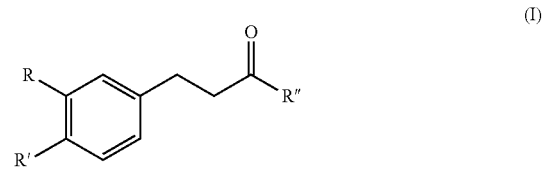

wherein
R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes

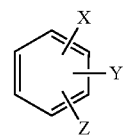

with X, Y and Z being independently of one another hydrogen, hydroxyl, an linear or branched $C_1$-$C_4$-alkyl group, or a linear or branched $OC_1$-$C_4$-alkyl group for stimulating biosynthesis of hyaluronan in human tissue or skin or hair.

INDUSTRIAL APPLICATION

More particularly the present invention also refers to a non-therapeutic method for stimulating the hyaluronan biosynthesis wherein at least one active compound of formula (I)

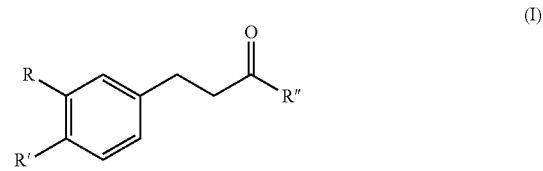

wherein
R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes

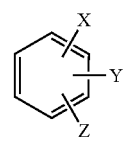

with X, Y and Z being independently of one another hydrogen, hydroxyl, an linear or branched $C_1$-$C_4$-alkyl group, or a linear or branched $OC_1$-$C_4$-alkyl group is administered to human tissue or skin or hair.

Also encompassed by the present invention is the use of at least one active compound of formula (I)

wherein
R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched C1-C9 alkyl group or A, wherein A denotes

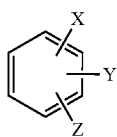

with X, Y and Z being independently of one another hydrogen, hydroxyl, an linear or branched $C_1$-$C_4$-alkyl group, or a linear or branched $OC_1$-$C_4$-alkyl group as stimulators for the biosynthesis of hyaluronan in human tissue or skin or hair.

Cosmetic Compositions

The compounds of formula (I) can easily be incorporated in the given concentrations in common cosmetic compositions such as pump sprays, aerosol sprays, creams, ointments, tinctures, lotions and the like without having an odorous, colouring or sensating effect. In this case, it is also possible and in many cases advantageous to combine the given hyaluronan biosynthesis stimulating compounds with further active ingredients.

The compositions according to the present invention can be produced by conventional processes known per se, such that one or more compounds of formula (I) are incorporated into products particularly for topical application which can have a conventional composition and which in addition to the effects mentioned hereinbefore or hereinafter can also be used for the treatment, care and cleansing of the skin or hair.

A preferred embodiment of the present invention relates to cosmetic compositions, comprising
(a) at least one active compound of formula (I)
(b) at least one cosmetic additive, preferably an anti-ageing additive, and
(c) at least one cosmetically acceptable carrier.

More particularly, the cosmetic additives are selected from the group consisting of
(b1) antioxidants;
(b2) primary or secondary sun protection factors, in particular substances which absorb or reflect UV radiation, preferably UV-filters (UV-absorbers) for cosmetic purposes, in particular for skin-protecting purposes;
(b3) matrix-metalloproteinase (MMP) inhibitors;
(b4) moisturizing agents, preferably selected from the group consisting of alkane diols or alkane triols;
(b5) glycosaminoglycans (GAGs) and further substances stimulating the synthesis of glycosaminoglycans;
(b6) anti-inflammatory agents;
(b7) TRPV1 antagonists;

A cosmetic composition, preferably a topical preparation according to the invention containing
(a) one or more active compounds of formula (I) and
(b) one or more anti-ageing actives selected from the above mentioned group of component (b1) to (b7)
allows to achieve an overall higher, i.e. more pronounced moisturizing and/or anti-ageing and/or wound healing promoting effect. Said more pronounced anti-ageing action is, at least partly, based on synergistic effects.

A cosmetic composition, preferably a topical preparation according to the invention containing
(a) one or more active compounds of formula (I) and
(b) one or more active ingredient selected from the above mentioned group of component (b)
have shown to exhibit particularly improved efficacy, in particular faster and/or stronger moisturizing and/or anti-ageing activity. In many cases a more than additive, often synergistic, activity was observed.

As mentioned above, HA can be significantly degraded by free radicals. The combination of one or more compounds of formula (I) and one or more antioxidants of component (b1) is particularly beneficial because antioxidants additionally protect HA from reactive oxygen species.

The combination of one or more compounds of formula (I) and one or more sun protection factors of component (b2) is particularly beneficial because UV light is one major source for reactive oxygen species. Furthermore as mentioned above, collagen fragments in the dermis resulting from UVB-induced collagen degradation were shown to cause loss of the pericellular HA matrix and strongly reduced HA secretion in human skin. Particular advantageous are therefore cosmetic, dermatological and/or pharmaceutical preparations according to the invention which additionally include one or more UV filters (UV absorbers) and which thus act as compositions with HA stimulating activity and additionally as a sunscreen, overall resulting in a higher, improved HA level.

MMP-1 cleaves collagen, resulting in the degradation of collagen. As mentioned above, collagen fragments resulting e.g. from the UVB-induced up-regulation of MMP-1 were shown to strongly reduced HA secretion in human skin. Particular advantageous are therefore cosmetic, dermatological and/or pharmaceutical preparations according to the invention which additionally include one or more matrix-metalloproteinase (MMP) inhibitor (b3) and which thus act as compositions with HA stimulating activity and additionally result in a higher, improved HA level due to reduced levels of collagen fragments.

The combination of one or more compounds of formula (I) and one or more skin moisturizing agents (b4) is particularly beneficial because skin moisturizing agents additionally improve the moisture status of the skin.

The combination of one or more compounds of formula (I) and one or more agents selected from the group consisting of glycosaminoglycans (GAGs) and further substances stimulating the synthesis of glycosaminoglycans (b5) is particularly beneficial resulting in an overall higher, improved GAG level.

It has been found rather advantageous to add the anti-ageing actives forming components (b1) to (b7) to the respective compositions in the following amounts:
the total quantity of antioxidants of component (b1) is in the range of from about 0.001 to about 10% b.w. preferably in the range of from about 0.01 to about 5% b.w., more preferably in the range of from about 0.05 to about 3% b.w. and/or
the total quantity of sun protection factors (UV filters and/or absorbers) of component (b2) is in the range of from about 0.01 to about 40% b.w., preferably in the range of from about 0.1 to about 30% by weight, more preferably in the range of from about 0.2 to about 20% by weight, even more preferably in the range of from about 0.5 to about 15% by weight, in particular in the range of from about 1.0 to about 10% by weight, and/or
the total quantity of matrix-metalloproteinase (MMP) inhibitors of component (b3) is in the range of from about 0.01 to about 5% b.w. preferably in the range of from about 0.01 to about 3% b.w. more preferably in the range of from about 0.05 to about 2% b.w. and/or
the total quantity of skin moisturizing agents of component (b4) is in the range of from about 0.1 to about 30% b.w, preferably in the range of from about 0.25 to about 20% b.w. more preferably in the range of from about 0.5 to about 10% b.w., even more preferably in the range of from about 1 to about 5% b.w. and/or the total quantity of glycosaminoglycans and substances stimulating the synthesis of glycosaminoglycans of component (b5) is in the range of from about 0.01 to about 10% b.w. preferably in the range of from about 0.05 to about 5% b.w., more preferably in the range of from about 0.1 to about 3% b.w., the total quantity of anti-inflammatory agents of component (b6) is in the range of from about 0.01 to about 10% b.w. preferably in the range of from about 0.05 to about 5% b.w., more preferably in the range of from about 0.1 to about 3% b.w., the total quantity of TRVP1 antagonists of component (b5) is in the range of from about 0.001 to about 5% b.w. preferably in the range of from about 0.01 to about 3% b.w., more preferably in the range of from about 0.05 to about 2% b.w., in each case based on the total weight of the composition.

Anti-Ageing Additives

In the context of the invention, anti-ageing or biogenic agents are, for example antioxidants, primary or secondary sun protection factors, matrix-metalloproteinase inhibitors (MMPI), skin moisturizing agents, glycosaminglycan stimulators, anti-inflammatory agents and TRPV1 antagonists.

(b1) Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysylthreonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

(b2) Primary and secondary sun protection factors. Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivative-sand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium)benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor
N-[(2 and 4)-[2-(oxoborn-3-ylidene)methyl]benzyl] acrylamide polymer
4,4'-[(6-[4-(1,1-dimethyl)aminocarbonyl)phenylamino]-1,3,5-triazine-2,4-diyl)-diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4''-(1,3,5-triazine-2,4,6-triyltriimino)tribenzoate (=2,4,6-trianilino-(p-carbo-2'-ethylhexyl-r-oxy)-1,3,5-triazine) (Uvinul® T150)
Broadband filters which are preferably combined with one or more compounds of formula (I) in a preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3(1,3,3,3-tetramethyl-1-(trime-thylsilyl)oxy) disiloxyanyl)propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2''-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2''-methylpropyloxy)-2-hydroxy}phenyl]-6-(4-methoxyphenyl)-1,3,5-triazine
UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/ (Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl)benzoic acid hexyl ester (Uvinul® A Plus)
indanylidene compounds in accordance with DE 100 55 940 A1 (=WO 2002 038537 A1)
UV filters which are more preferably combined with one or more compounds of formula (I) in a preparation according to the present invention are selected from the group consisting of
p-aminobenzoic acid
3-(4'-trimethylammonium)benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene)methyl]benzyl] acrylamide polymer
p-methoxycinnamic acid-2-ethylhexyl ester (Neo Heliopan® AV)

p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3(1,3,3,3-tetramethyl-1-(trimethylsilyl)oxy) disiloxyanyl)propyl) (Mexoryl® XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl)benzoic acid hexyl ester (Uvinul® A Plus)
indanylidene compounds in accordance with DE 100 55 940 (=WO 20202 038537 A1).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta, hexa- and heptathionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

(b3) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 2002 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

(b4) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

(b5) Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

(b6) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willowherb, oats, *calendula, arnica*, St John's wort, honeysuckle, rosemary, *Passiflora incarnata*, witch hazel, ginger or *Echinacea*; preferably selected from the group consisting of extracts or fractions from camomile, Aloe vera, oats, *calendula, arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-) ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

(b7) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

In case vitamin A and/or a derivative of vitamin A is used as component (b1) or as constituent of component (b1), the total amount thereof preferably is in the range of from 0.1 to 3% b.w., based on the total weight of the preparation.

In case vitamin E and/or a derivative of vitamin E is used as component (b1) or as constituent(s) of component (b1), the total amount thereof preferably is in the range of from 0.1 to 2% b.w., based on the total weight of the preparation.

In case vitamin C and/or a derivative of vitamin C is used as component (b1) or as constituent of component (b–1), the total amount thereof preferably is in the range of from 0.01 to 3% b.w., based on the total weight of the preparation.

In case ubiquinone is used as component (b1) or as constituent of component (b1), the total amount thereof preferably is in the range of from 0.001 to 0.1% b.w., based on the total weight of the preparation.

In case hyaluronic acid and/or a derivative or salt of hyaluronic acid is used as component (b5) or as constituent of component (b5), the total amount thereof preferably is in the range of from 0.01 to 3% b.w., based on the total weight of the preparation.

In case Retinol and/or a derivative of retinol is used as component (b5) or as constituent of component (b5), the total amount thereof preferably is in the range of from 0.01 to 1% b.w., based on the total weight of the preparation.

In case alpha-bisabolol (natural or synthetic) is used as component (b5) or as constituent of component (b5), the total amount thereof preferably is in the range of from 0.01 to 0.5% b.w., based on the total weight of the preparation.

In case oat glucan is used as component (b5) or as constituent of component (b5), the total amount thereof preferably is in the range of from 0.01 to 1% b.w., based on the total weight of the preparation.

In case *Echinacea purpurea* extract is used as component (b5) or as constituent of component (b5), the total amount thereof preferably is in the range of from 0.1 to 0.6% b.w., based on the total weight of the preparation.

In case *Alpinia galanga* leaf extract is used as component (b5) or as constituent of component (b5), the total amount thereof preferably is in the range of from 0.1 to 5% b.w., based on the total weight of the preparation.

In case *Sinorhizobium Meliloti* Ferment Filtrate is used as component (b5) or as constituent of component (b-5), the total amount thereof preferably is in the range of from 0.1 to 5% b.w., based on the total weight of the preparation.

In case Tetradecyl Aminobutyroylvalylaminobutyric Urea Trifluoroacetate is used as component (b5) or as constituent of component (b5), the total amount thereof preferably is in the range of from 0.1 to 3% b.w., based on the total weight of the preparation.

In case Retinyl palmitate is used as component (b3) or as constituent of component (b-3), the total amount thereof preferably is in the range of from 1 to 3% b.w., based on the total weight of the preparation.

In case Ursolic acid is used as component (b3) or as constituent of component (b-3), the total amount thereof preferably is in the range of from 0.01 to 1% b.w., based on the total weight of the preparation.

In case one or more than one extract from the leaves of the Rosaceae family, sub-family Rosoideae is used as component (b3) or as constituent of component (b-3), the total amount thereof preferably is in the range of from 0.01 to 3% b.w., based on the total weight of the preparation.

In case Genistein and/or Daidzein is used as component (b3) or as constituent of component (b3), the total amount thereof preferably is in the range of from 0.01 to 2% b.w., based on the total weight of the preparation.

Additional Cosmetic Additives

The preparations according to the invention may also contain surfactants, oil bodies, emulsifiers, superfatting agents, pearlising waxes, consistency factors, polymers, silicone compounds, waxes, stabilizers, antidandruff agents, film formers, swelling agents, hydrotropes, preservatives, solubilizers, complexing agents, reducing agents, alkalising agents, perfume oils, dyes and the like as additional auxiliaries and additives.

A. Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

B. Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

C. Emulsifiers

Other surfactants may also be added to the preparations as emulsifiers, including for example:

- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

(i) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(ii) Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(iii) Polyglycerol esters. Typical examples of suitable polyglycerol esters are Polyglyceryl® 2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

(iv) Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

(v) Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

D. Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

E. Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

F. Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

G. Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

H. Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

I. Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

J. Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxyl)acetate, menthyl-(2-methoxyethoxy-)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, l-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

K. Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

L. Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

M. Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniper-berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxy-allantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

N. Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

O. Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

R. Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

S. Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, •-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

T. Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3Fe_3O_4$, FeO(OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after-sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation. It should be noted that the information on additives and their ranges for cosmetic compositions are also valid for pharmaceutical or dermatological formulations.

Encapsulation

Although one preferred embodiment of the present invention relates to topical application, the compositions may also be administered orally, preferably in the form of a capsule. The compositions are typically encapsulated by means of a solid covering material, which is preferably selected from starches, degraded or chemically or physically modified starches (in particular dextrins and maltodextrins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0389700 A1, U.S. Pat. No. 4,251,195, U.S. Pat. No. 6,214,376, WO 2003 055587 or WO 2004 050069 A1.

The capsules, however, may also represent micro-capsules. "Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

The active principles are released from the microcapsules by mechanical, thermal, chemical or enzymatic destruction of the membrane, normally during the use of the preparations containing the microcapsules. Despite the fact that the state of the art a huge range of possibilities for the encapsulation of actives, methods according to which a shell is obtained by coazervation, precipitation or polycondensation of anionic and cationic polymers has been quite suitable for the formation of stable capsules. Particularly, a preferred process for the encapsulation of active principles according to the present invention is characterised in that it comprises the steps of (a) preparing a matrix from gel formers, cationic polymers and active principles;
(b) optionally dispersing said matrix in an oil phase; and
(c) treating said dispersed matrix with aqueous solutions of anionic polymers and optionally removing the in phase in the process.

Of course, anionic and cationic polymers in steps (a) and (c) can be exchanged.

(i) Gel formers. In the context of the invention, preferred gel formers are substances which are capable of forming gels in aqueous solution at temperatures above 40° C. Typical examples of such gel formers are heteropolysaccharides and proteins. Preferred thermogelling heteropolysaccharides are agaroses which may be present in the form of the agar agar obtainable from red algae, even together with up to 30% by weight of non-gel-forming agaropectins. The principal constituent of agaroses are linear polysaccharides of Galactose and 3,6-anhydro-L-galactose with alternate 1,3- and 1,4-glycosidic bonds. The heteropolysaccharides preferably have a molecular weight of 110,000 to 160,000 and are both odourless and tasteless. Suitable alternatives are pectins, xanthans (including xanthan gum) and mixtures thereof. Other preferred types are those which in 1% by weight aqueous solution still form gels that do not melt below 80° C. and solidify again above 40° C. Examples from the group of thermogelling proteins are the various gelatines.

(ii) Anionic polymers. Salts of alginic acid are preferred for this purpose. The alginic acid is a mixture of carboxyl-containing polysaccharides with the following idealized monomer unit:

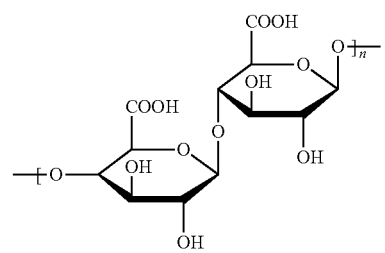

The average molecular weight of the alginic acid or the alginates is in the range from 150,000 to 250,000. Salts of alginic acid and complete and partial neutralization products thereof are understood In particular to be the alkali metal salts, preferably sodium alginate ("algin") and the ammonium and alkaline earth metal salts. Mixed alginates, for example sodium/magnesium or sodium/calcium alginates, are particularly preferred. In an alternative embodiment of the invention, however, carboxymethyl celluloses and anionic chitosan derivatives, for example the carboxylation and above all succinylation products are also suitable for this purpose.

(iii) Cationic polymers. Chitosans are biopolymers which belong to the group of hydrocolloids. Chemically, they are partly de-acetylated chitins differing in their molecular weights which contain the following—idealized—monomer unit:

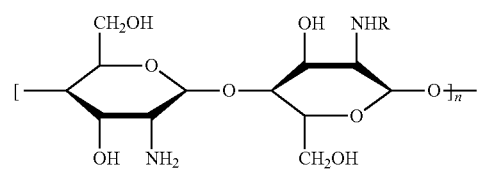

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations.

In a preferred embodiment of the invention a 1 to 10 and preferably 2 to 5% by weight aqueous solution of the gel former, preferably agar agar, is normally prepared and heated under reflux. A second aqueous solution containing the cationic polymer, preferably chitosan, in quantities of 0.1 to 2 and preferably 0.25 to 0.5% by weight and the active principle in quantities of 0.1 to 25 and preferably 0.25 to 10% by weight is added in the boiling heat, preferably at 80 to 100° C.; this mixture is called the matrix. Accordingly, the charging of the microcapsules with active principles may also comprise 0.1 to 25% by weight, based on the weight of the capsules. If desired, water-insoluble constituents, for example inorganic pigments, may also be added at this stage to adjust viscosity, generally in the form of aqueous or aqueous/alcoholic dispersions. In addition, to emulsify or disperse the active principles, it can be useful to add emulsifiers and/or solubilisers to the matrix. After its preparation from gel former, cationic polymer and active principle, the matrix optionally is very finely dispersed in an oil phase with intensive shearing in order to produce small particles in the subsequent encapsulation process. It has proved to be particularly advantageous in this regard to heat the matrix to temperatures in the range from 40 to 60° C. while the oil phase is cooled to 10 to 20° C. The actual encapsulation, i.e. formation of the membrane by contacting the cationic polymer in the matrix with the anionic polymers, takes place in the third step. To this end, it is advisable to wash the matrix—dispersed in the oil phase—with an aqueous ca. 0.1 to 3 and preferably 0.25 to 0.5% by weight aqueous solution of the anionic polymer, preferably the alginate, at a temperature in the range from 40 to 100 and preferably 50 to 60° C. and, at the same time, to remove the oil phase if present. The resulting aqueous preparations generally have a microcapsule content of 1 to 10% by weight. In some cases, it can be of advantage for the solution of the polymers to contain other ingredients, for example emulsifiers or preservatives. After filtration, microcapsules with a mean diameter of preferably 1 to 3 mm are obtained. It is advisable to sieve the capsules to ensure a uniform size distribution. The microcapsules thus obtained may have any shape within production-related limits, but are preferably substantially spherical.

EXAMPLES

Example 1

Cellular In Vitro Hyaluronan Assay on Normal Human Dermal Fibroblasts (NHDF)

NHDF are seeded into a 24 well plate at a concentration of $1.5 \times 10^4$ cells/well. Cells are incubated at 37° C. and 5% $CO_2$ in fibroblast medium containing 10% fetal bovine serum (FBS) until they are 70-80% confluent. Then the medium is withdrawn, cells are washed with PBS and the test compounds dissolved in fibroblast medium without FBS are added. After incubation for 16 h in the presence of the test compounds, the culture medium is collected and hyaluronan is determined by a hyaluronic acid ELISA detection kit (Corgenix) which is performed according to the supplier instructions. The stimulation of the hyaluronan biosynthesis in the presence of the test compounds is calculated according to the following equation:

Hyaluronan stimulation [%]=($HA_{control}$/$HA_{test\ compound}$×100)−100 with $HA_{control}$=hyaluronan content in ng/ml of the medium from cells treated with control
$HA_{test\ compound}$=hyaluronan content in ng/ml of the medium from cells treated with test compound
The results are presented in Table 1.

TABLE 1

Mean hyaluronan stimulation versus control in vitro/NHDF

| Test compound | Test concentration [µM] | Mean hyaluron stimulation vs. control |
|---|---|---|
| Retinoic acid | 0.1 | −13.0 ± 18.0 |
| Retinol | 0.1 | 2.0 |
| TGF-b1 | 1 ng/ml | 39.7 ± 13.9 |
| Compound of formula IV | 0.25 | −5.5 ± 2.5 |
| Zingerone | 0.25 | 15.0 ± 5.3 |
| Cassione | 0.25 | 41.0 ± 6.0 |
| [6]-Paradol | 0.025 | 38.0 ± 9.0 |

The results clearly show that zingerone, cassione and [6]-paradol all three enhance the hyaluronan production of NHDF whereas compound of formula IV and the two references retinoic acid and retinol exhibit no stimulatory activity on the hyaluronan biosynthesis of dermal fibroblasts. The mean hyaluronan stimulation of cassione at 0.25 µM and [6]-paradol at 0.025 µM is comparable to that of the positive control TGF-b1 tested at 1 ng/ml.

Example 2

Cellular In Vitro Hyaluronan Assay on Normal Human Epidermal Keratinocytes (NHEK)

NHEK are seeded into a 24 well plate at a concentration of $2.5 \times 10^4$ cells/well. Cells are incubated at 37° C. and 5% $CO_2$ in keratinocyte medium until they are 70-80% confluent. Then the medium is withdrawn, cells are washed with PBS and the test compounds dissolved in keratinocyte medium are added. After incubation for 16 h in the presence of the test compounds, the culture medium is collected and hyaluronan is determined by a hyaluronic acid ELISA detection kit (Corgenix) which is performed according to the supplier instructions. The stimulation of the hyaluronan biosynthesis in the presence of the test compounds is calculated according to the following equation:

Hyaluronan stimulation [%]=($HA_{control}$/$HA_{test\ compound}$×100)−100 with $HA_{control}$=hyaluronan content in ng/ml of the medium from cells treated with control
$HA_{test\ compound}$=hyaluronan content in ng/ml of the medium from cells treated with test compound
The results are presented in Table 2.

TABLE 2

Mean hyaluronan stimulation versus control/NHEK

| Test compound | Test concentration [µM] | Mean hyaluron stimulation vs. control |
|---|---|---|
| Retinoic acid | 0.1 | 116.1 ± 37.3 |
| Retinol | 0.1 | 70.8 ± 33.3 |
| TGF-b1 | 1 ng/ml | −31.0 |
| Compound of formula IV | 0.25 | 50.5 ± 26.5 |
| Zingerone | 0.25 | 45.0 ± 24.7 |
| Cassione | 0.25 | 37.0 ± 8.0 |
| [6]-Paradol | 0.025 | −3.0 ± 3.0 |

The results clearly show that compound of formula IV, zingerone and cassione all three enhance the hyaluronan production of NHEK whereas [6]-paradol and the references TGF-b1 exhibit no stimulatory activity on the hyaluronan biosynthesis of epidermal keratinocytes. The mean hyaluronan stimulation of compound of formula IV, zingerone and cassione all tested at 0.25 µM is only 1.4, 1.6 and 1.9 fold less than that of the positive control retinol tested at 0.1 µM.

The data of Tables 1 and 2 show that compounds of formula (I) according to the present invention have a potent hyaluronan synthesis stimulating effect on human skin cells in vitro.

Example 3

Hyaluronan Assay on Ex Vivo Human Skin

Human skin obtained from plastic surgery is cut into pieces of approximately 7×3 mm (diameter×thickness). 6 skin samples are used for each treatment. The skin samples are placed on a cotton pad soaked with culture medium (modified Williams'E medium). Control and hydrodispersion gels (as described in more detail below) without (=placebo) and with the test compound, respectively, are applied topically on day 0 and the application is renewed on day 1. On day 2, skin samples are fixed, histological sections are prepared and subsequent histochemically stained by Alcain blue. After that, pictures are taken from each section and dermal and epidermal hyaluronan is quantified by image analysis of a selected region of interest. To do so, the histochemical staining is divided in three different color channels with an algorithm specific for Alcain blue staining and the distribution and intensity of the blue colour channel which is specific for hyaluronan is analysed.

Hyaluronan stimulation [%]=($HA_{control}$/$HA_{test\ compound}$×100)−100 with $HA_{control}$=hyaluronan score of the skin sample treated with control
$HA_{test\ compound}$=hyaluron score of the skin sample treated with test compound The results are presented in Table 3.

TABLE 3

Mean hyaluronan stimulation versus control/ex vivo human skin

| Test compound | Test concentration [%] | Mean hyaluronan stimulation vs. control [%] Dermal | Epidermal |
|---|---|---|---|
| Placebo | — | −36 | −37 |
| [6]-Paradol | 0.0001 | 124 | 51 |

The examples show that [6]-Paradol at 0.0001% significantly stimulates the dermal and very surprisingly also the epidermal hyaluronan level of ex vivo human skin after only 2 days of topically treatment whereas the placebo results in an inhibition of the dermal and also the epidermal HA.

Mean HA stimulation of the 0.0001% [6]-paradol containing gel versus placebo is 250% for dermal HA and 124% for epidermal HA.

These data show that compounds of formula (I) according to the present invention have a hyaluronan biosynthesis stimulating effect on ex vivo skin. The hydrodispersion gels used had the composition as set out in Table 4:

TABLE 4

Composition hydrodispersion gels (amounts in % b.w.)

| Raw material | INCI | Gel A | Gel B |
|---|---|---|---|
| [6]-Paradol | Hydroxymethoxyphenyl Decanone | \ | 0.0001 |
| PCL Liquid 100 | Cetearyl Octanoate | 3.0 | 3.0 |
| Lanette O | Cetearyl Alcohol | 2.0 | 2.0 |
| Paraffinoil 5°E | Mineral Oil | 3.0 | 3.0 |
| Eutanol G | Octyldodecanol | 4.0 | 4.0 |
| Abil 350 | Dimethicone | 0.5 | 0.5 |
| Pemulen TR1 | Acrylates/C10-30 Alkyl Acrylate Crosspolymer | 0.2 | 0.2 |
| Ultrez-21 | Acrylates/C10-30 Alkyl Acrylate Crosspolymer | 0.05 | 0.05 |
| NaOH-Sol. 10% | Sodium Hydroxide | 0.5 | 0.5 |
| Hydrolite-5 | 1,2 Pentylene Glycol | 2.0 | 2.0 |
| Water | Water (Aqua) | ad 100 | ad 100 |
|  | pH value of the formulation | 6.2 | 6.2 |

Example 4

Formulation Examples

Table 5 presents a number of formulations according to the invention
1=Skin calming balm
2=Tinted Anti-Aging Balm, SPF 15
3=After-sun moisturizing spray O/W
4=Night cream W/O
5=Anti-wrinkle moisturizing ampoule
6=After-Shave Hydrogel
7=Hair shampoo
8=Antiperspirant pump spray
9=Skin lightening day care fluid O/W
10=Barrier repair cream O/W
11=Sun protection lotion SPF 24 (UVA/UVB Balance)

As far as the [6]-paradol, cassione, zingerone and compound of formula IV concentrations are concerned, the abbreviation for the concentrations have the following meaning:

| | | | |
|---|---|---|---|
| 1-4 = 0.0001 | 1-3 = 0.001 | 1-2 = 0.01 | 1-1 = 0.1 |
| 2-4 = 0.0002 | 2-3 = 0.002 | 2-2 = 0.02 | 2-1 = 0.2 |
| 3-4 = 0.0003 | 3-3 = 0.003 | 3-2 = 0.03 | 3-1 = 0.3 |
| 4-4 = 0.0004 | 4-3 = 0.004 | 4-2 = 0.04 | 4-1 = 0.4 |
| 5-4 = 0.0005 | 5-3 = 0.005 | 5-2 = 0.05 | 5-1 = 0.5 |

TABLE 5

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| Cassione |  |  |  |  |  | 3-3 |  |  |  |  |  |
| Compound of formula IV |  |  | 5-3 |  |  |  |  |  | 1-2 |  |  |
| [6]-Paradol Hydroxymethoxyphenyl Decanone |  | 5-4 |  |  |  |  |  |  | 1-4 |  | 1-4 |
| [6]-Paradol 1% solution in propylen glycol Propylene Glycol, Hydroxymethoxyphenyl Decanone |  |  |  |  | 2-2 | 5-1 |  |  |  |  | 5-2 |
| [6]-Paradol 0.2% solution in oil Caprylic/Capric Triglyceride, Hydroxymethoxyphenyl Decanone | 5-1 |  |  | 2-1 |  |  |  |  |  |  |  |

TABLE 5-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| [6]-paradol absolut | 1-3 | 5-4 | | 4-4 | | 2-4 | 5-3 | 1-4 | | 1-4 | 5-4 |
| Zingerone | | | 5-3 | | | | | | | 5-4 | |
| Actipone Laminaria Saccharina Glycerin, Water (Aqua), Laminaria Saccharina Extract | | | | | | 0.3 | | | | | |
| Allantoin | 0.1 | | | | | 0.1 | | | | | |
| Aloe Barbadensis Leaf Juice | | | | | | | | | | | 1 |
| Aluminium Stearate | | | | 1.2 | | | | | | | |
| Arbutin | | | | | | | | | 1 | | |
| Arlypon ® F Laureth-2 | | | | | | | 2 | | | | |
| Avocado Öl | | | | 3 | | | | | | | |
| Betulin 90% | | | | | | | | | | 0.1 | |
| Biotive L-Arginine | | 0.6 | | | | | | | | | 0.5 |
| Biotive Troxerutin | | 0.5 | | | | | | | | | 0.5 |
| (-)-alpha-Bisabolol | | | | | | | | | | 0.1 | |
| Carbopol ® Ultrez-10 Carbomer | | 0.2 | | | | 0.4 | | | 0.2 | | |
| CeramideBIO ® Cetylhydroxyproline Palmitamide | | | | | | | | | | 0.5 | |
| Citric acid 10% in water | | | | | | | 0.5 | | | | |
| Covi-Ox ® T-70 Tocopherol | | | 0.1 | | | | | | | | |
| Crinipan ® AD Climbazole | | | | | | | 0.3 | | | | |
| Cutina ® PES Pentae-rythrityl Distearate | | 2 | | | | | | | | | |
| D-Panthenol | 1 | | 1 | | 1 | 0.5 | 0.5 | | | | |
| Dermacryl ® AQF Acrylates Copolymer | | | | | | | | | | | 2 |
| Dow Corning 200(100cs) Silicone Fluid Dimethicone | 2 | 2 | | | | | | | 0.5 | 0.5 | |
| Dow Corning 246 Fluid Cyclohexasiloxane, Cyclopentasiloxane | | | | 2 | | | | | | | 3 |
| Dracorin ® CE Glyceryl Stearate Citrate | | | | | | | | | | 1.5 | |
| Dracorin ® GMS Glyceryl Stearate | | | | | | | | | | 2 | |
| Dracorin ® GOC lyceryl Oleate Citrate, Caprylic/Capric Triglyceride | | | | 2 | | | | | | | |
| Dragocalm ® Water (Aqua), Glycerin, Avena Sativa (Oat) Kernel Extract | | | | | 1 | | | | | | |
| Dragocid ® Liquid Phenoxyethanol, Methylparaben, Ethylparaben, Butylparaben, Propylparaben, Isobutylparaben | | | | | | | | | 0.8 | | |
| Dragoderm ® Glycerin, Triticum Vulgare (Wheat) Gluten, Water (Aqua) | | | | | | | 0.5 | | | | |
| Dragosan ® W/O P Sorbitan Isostearate, Hydrogenated Castor Oil, Ceresin, Beeswax (Cera Alba) | | | | 8 | | | | | | | |
| Dragosantol ® 100 Bisabolol | | 0.1 | | | | 0.1 | | | | | |
| Dragosine ® Carnosine | | | | | 0.2 | | | | | | |
| Dragoxat ® 89 Ethylhexyl Isononanoate | | 5 | | 7 | | | | | | 2 | 2 |
| Disodium EDTA | 0.1 | 0.1 | | | | | | | 0.1 | | 0.1 |
| Emulsiphos ® Potassium Cetyl Phosphate, Hydrogenated Palm Glycerides | | 2 | | | | | | | 1.5 | 2 | 2 |

TABLE 5-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| Ethanol | | | 5 | | | 8 | | | | | |
| Extrapone ® Aloe vera Water (Aqua), Aloe Barbadensis, Propylene Glycol, Alcohol | | | | | | 2 | | | | | |
| Extrapone ® Witch Hazel Propylene Glycol, Hamamelis Virginiana (Witch Hazel) Water, Water (Aqua), Hamamelis Virginiana (Witch Hazel) Extract | 1 | | | | | | | | | | |
| Extrapone ® Rosemary Glycerin, Water (Aqua), Rosmarinus Officinalis (Rosemary) Leaf Extract | | | | | | | 0.3 | | | | |
| Extrapone ® Seaweed Water (Aqua), Butylene Glycol, Fucus Vesiculosus Extract | | | | | | 0.5 | | | | | |
| Food Color Brown E172 + E171 Powder | | 2 | | | | | | | | | |
| Frescolat ® MGA Menthone Glycerin Acetal | | | | | 0.1 | | | | | | |
| Frescolat ® ML Menthyl Lactate | | | 0.5 | | | 0.3 | 0.2 | | | | |
| Genapol ® LRO Liquid Sodium Laureth Sulfate | | | | | | | | 37 | | | |
| Givobio ® GZN Zinc Gluconate | | | | | | | | | | 0.5 | |
| Glycerol | 1.5 | | 4 | 3 | | | | | 3.5 | 3 | 3 |
| Hydrolite ® 5 Pentylene Glycol | 3 | | 5 | | | 5 | | 5 | | | 2 |
| Hydroviton-24 ® Water (Aqua), Pentylene Glycol, Glycerin, Lactic Acid, Sodium Lactate, Serine, Urea, Sorbitol, Sodium Chloride, Allantoin | | | | 1 | | | | | | | |
| Hydroviton ® Plus 2290 Water (Aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | | | | | | | | 1 | 2 | |
| Isoadipate Diisopropyl Adipate | | | | | | | | | 2 | | |
| Isodragol ® Triisononanoin | 1 | | | | | | | | | 3 | 2 |
| Jojoba Oil | | | | 2 | | | | | | | |
| Potassium sorbate | | | 0.1 | | | | | | | | |
| Keltrol ® CG-RD Xanthan Gum | | 0.2 | | | 0.05 | | | | 0.2 | | 0.4 |
| Kojic acid | | | | | | | | | 0.5 | | |
| Lanette ® 16 Cetyl Alcohol | | | | | | | | | 1.5 | | 1 |
| Lanette ® O Cetearyl Alcohol | | | | | | | | | | 2 | 0.5 |
| Lara Care ® A-200 Galactoarabinan | | | | | | | | | | | 0.3 |
| Locron ® L Aluminium Chlorohydrate | | | | | | | | 16 | | | |
| Magnesium Sulfate | | | | 0.7 | | | | | | | |
| Mineral Oil | | | | 8 | | | | | | | |
| Sodium Ascorbyl Phosphate | | | | | | | | | 1 | | |
| Sodium Chloride | | | | | | | 0.1 | | | | |
| Sodium hydroxide | 1 | | | | | 0.75 | | | 0.2 | 0.3 | |
| Neo Heliopan ® 303 Octocrylene | | 4 | | | | | | | | | 10 |
| Neo Heliopan ® 357 Butylmethoxydibenzoylmethane | | 2 | | | | | | | 2 | | 3 |
| Neo Heliopan ® AP, 15% Lösung, neutralisiert mit L-Arginin | | 6.7 | | | | | | | | | 6.7 |

TABLE 5-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| Aqua, Disodium Phenyl Dibenzimidazole Tetrasulfonate, Arginin |  |  |  |  |  |  |  |  |  |  |  |
| Neo Heliopan ® AV Ethylhexyl Methoxycinnamate |  |  |  |  |  |  |  |  | 7.5 |  |  |
| Neo Heliopan ® BB Benzophenone-3 |  |  |  |  |  |  |  |  | 3 |  |  |
| Neo Heliopan ® E 1000 Isoamyl p.Methoxycinnamate |  |  |  |  |  |  |  |  |  |  | 1 |
| Neo Heliopan ® HMS Homosalate |  |  |  |  |  |  |  |  | 10 |  | 5 |
| Neo Heliopan ® Hydro, 20% Lösung, neutralisiert mit Biotive Arginine Aqua, Phenylbenzimidazole, Sulphonic Acid, Arginin |  | 10 |  |  |  |  |  |  |  |  | 10 |
| Neo Heliopan ® OS Ethylhexyl Salicylate |  | 3 |  |  |  |  |  |  | 5 |  |  |
| Neo-PCL Water Soluble N Trideceth-9, PEG-5 Ethylhexanoate, Water (Aqua) |  |  |  |  |  | 1 | 1.5 | 2 |  |  |  |
| Neutralöl Caprylic/Capric Triglyceride |  |  | 5 |  |  |  |  |  |  | 10 |  |
| Ozokerite Wax 2389 |  |  |  | 2 |  |  |  |  |  |  |  |
| Parfume oil | 0.2 | 0.3 | 0.25 | 0.3 | 0.1 | 0.1 | 0.5 | 1.0 | 0.3 | 0.1 | 0.2 |
| PCL-Liquid 100 Cetearyl Ethylhexanoate | 3 | 2 | 4 | 5 |  |  |  |  |  |  |  |
| PCL-Solid Stearyl Heptanoate, Stearyl Caprylate | 1 |  | 0.5 |  |  |  |  |  |  |  |  |
| Pemulen ® TR-2 Acrylates/C10-30 Alkyl Acrylate Crosspolymer | 0.6 |  | 0.25 |  |  |  |  |  |  |  |  |
| Phytoconcentrole ® Shea Butter Glycine Soja (Soybean) Oil, Butyrospermum Parkii (Shea Butter) | 1 |  |  |  |  |  |  |  |  |  |  |
| Polymer JR 400 Polyquaternium-10 |  |  |  |  |  |  | 0.4 |  |  |  |  |
| Propylenglycol-1,2 Propylene Glycol |  |  |  |  | 5 |  |  |  |  |  |  |
| Silcare Silicone 41M65 Stearyl Dimethicone |  |  |  |  |  |  |  |  |  |  | 1 |
| Solubilizer PEG-40 Hydrogenated Castor Oil, Trideceth-9, Propylene Glycol, Water (Aqua) |  |  |  |  | 1.5 |  |  | 3 |  |  |  |
| SymCalmin ® Butylene Glycol, Pentylene Glycol, Hydroxyphenyl Propamidobenzoic Acid | 1 |  |  |  |  |  | 0.1 |  |  | 0.1 |  |
| SymClariol ® Decylene Glycol |  | 0.5 |  |  |  |  |  |  | 0.3 |  |  |
| SymDeo ® B125 2-Methyl 5-Cyclohexylpentanol |  |  |  |  |  |  |  |  | 0.2 |  |  |
| SymDeo ® MPP Dimethyl Phenyl 2-Butanol |  |  |  |  |  |  |  |  | 0.5 |  |  |
| Symdiol ® 68 1.2-Hexanediol, Caprylyl Glycol | 1 |  |  |  | 1 |  |  |  |  |  |  |
| SymFinity ® 1298 Echinacea Purpurea Extract |  |  |  |  | 0.06 |  |  |  |  |  |  |
| SymGlucan ® Water (Aqua), Glycerin, Beta-Glucan | 1 |  | 1 |  | 5 |  |  |  |  |  | 2 |
| SymHelios 1031 Benzylidene Dimethoxydimethylindanone |  | 0.5 |  |  |  |  |  |  |  |  |  |
| SymMatrix Maltodextrin, Rubus Fruticosus (Blackberry) Leaf Extract |  | 0.2 |  |  | 0.1 |  |  |  |  |  |  |

TABLE 5-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| SymMollient ® W/S Trideceth-9, PEG-5 Isononanoate, Water (Aqua) | | | | | 2 | | | | | | |
| SymOcide ® PS Phenoxyethanol, Decylene Glycol, 1,2-Hexanediol | | | | | | | 1.0 | | | 0.8 | |
| SymOcide ® PT Phenoxyethanol, Tropolone | | | | 0.8 | | | | | | | |
| SymRelief ® 100 Bisabolol, Zingiber Officinale (Ginger) Root Extract | | | | | | | 0.2 | | | | 0.1 |
| SymRepair ® Hexyldecanol, Bisabolol, Cetylhydroxyproline Palmitamide, Stearic Acid, Brassica Campestris (Rapeseed) Sterols | | 1 | | 3 | | | | | | | |
| SymSol ® PF-3 Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | | | | | | 1.3 | | | | | |
| SymSitive ® 1609 Pentylene Glycol, 4-t-Butylcyclohexanol | | | 0.5 | | | | | | 0.5 | | |
| SymVital ® Aloe Barbadensis Leaf Juice Powder, Magnesium Ascorbyl Phosphate, Rubus Idaeus (Raspberry) Leaf Extract | | | | | 0.1 | | | | | | |
| SymWhite ® 377 Phenylethyl Resorcinol | | | | | | | | | 0.5 | | |
| Tamasterol ® Phytosterols | | | | | | | | | | 0.3 | |
| Tapioca Pure Tapioca Starch | | | | | | | | | | | 5 |
| Tego Betain ® L7 Cocamidopropyl Betain | | | | | | | | 8 | | | |
| Tegosoft ® PC 31 Polyglyceryl-3 Caprate | | | | | | | | | | 0.3 | |
| Tegosoft ® TN C12-C15 Alkyl benzoate | | | | | | | | | | | |
| Triethanolamine | | | | 0.3 | | | | | | | |
| Vitamin A Palmitat Retinyl Palmitate | | | | | | 0.1 | | | | | |
| Vitamin E Acetat Tocopheryl Acetate | | 0.5 | | 0.2 | | | | | | 0.3 | 0.5 |
| Water | | | | | | Ad 100 | | | | | |

Example 5

Gel dental cream

| Ingredient | I (%) | II (%) | III (%) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Peppermint aroma | 1.00 | 1.00 | 1.00 |
| [6]-Paradol | 0.003 | | |
| Zingerone | | 0.005 | |
| Compound of formula IV | | | 0.02 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | to 100.00 | to 100.00 | to 100.00 |

Example 6

Chewing gum

| Ingredient | I (%) | II (%) | III (%) |
|---|---|---|---|
| Chewing gum base | 21.00 | 21.00 | 21.00 |
| Glucose syrup | 16.50 | 16.50 | 16.50 |

-continued

| Chewing gum | | | |
|---|---|---|---|
| Ingredient | I (%) | II (%) | III (%) |
| Glycerin | 0.50 | 0.50 | 0.50 |
| Powdered sugar | 60.45 | 60.36 | 60.27 |
| Spearmint aroma | 1.50 | 1.50 | 1.50 |
| [6]-Paradol | 0.001 | | |
| Zingerone | | 0.005 | |
| Compound of formula IV | | | 0.01 |

Example 7

Ready-to-Use Mouthwash with Fluoride

| Ingredient | I (%) | II (%) | III (%) |
|---|---|---|---|
| Ethanol | 7.00 | 7.00 | 7.00 |
| Glycerin | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Cinnamon/menthol aroma | 0.15 | 0.15 | 0.15 |
| [6]-Paradol | 0.002 | | |
| Cassione | | 0.01 | |
| Compound of formula IV | | | 0.005 |
| Dyestuff | 0.01 | 0.01 | 0.01 |
| Dist. water | to 100.00 | to 100.00 | to 100.00 |

The invention claimed is:

1. A cosmetic composition, comprising active compounds of formula (I)

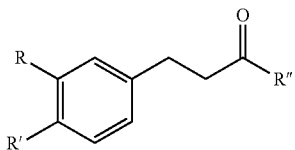

wherein

R and R' independently of one another denote, hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes

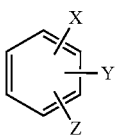

with X, Y and Z being independently of one another hydrogen, hydroxyl, an linear or branched $C_1$-$C_4$-alkyl group, or a linear or branched $OC_1$-$C_4$-alkyl group, and wherein the actives are present in amounts of 0.000005 to 0.00001 percent by weight based on the total weight of the composition.

2. The composition of claim 1, wherein the active is 4-(3,4-methylendioxyphenyl)-2-butanone (Cassione) according to formula (II)

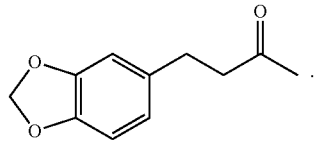

3. The cosmetic composition of claim 1, comprising
(a) at least ore active of formula (I),
(b) at least one cosmetic additive, and
(c) at least one cosmetically acceptable carrier.

4. The composition of claim 3, wherein said cosmetic additives are selected from the group consisting of antioxidants, primary or secondary sun protection factors, matrix-metalloproteinase (MMP) inhibitors, skin-moisturizing agents, glycosaminoglycans (GAGs) and further substances stimulating the synthesis of glycosaminoglycans, anti-inflammatory agents and TRVP1 antagonists.

5. The composition of claim 3 for topical application.

6. The composition of claim 3 for oral administration.

7. A pharmaceutical or dermatological composition, comprising active compounds of formula (I)

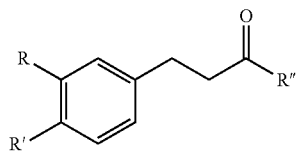

wherein

R and R' independently of one another denote hydrogen, hydroxyl, a linear or branched $OC_1$-$C_4$-alkyl group, or optionally R and R' form together a methylenedioxy group resulting in a 3,4-methylendioxyphenyl residue and R" denotes a linear or branched $C_1$-$C_9$ alkyl group or A, wherein A denotes

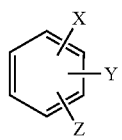

with X, Y and Z being independently of one another hydrogen, hydroxyl, an linear or branched $C_1$-$C_4$-alkyl group, or a linear or branched $OC_1$-$C_4$-alkyl group for stimulating biosynthesis of hyaluronan in human tissue or skin or hair.

8. The composition of claim 7 wherein the actives are present in amounts of 0.000005 to 0.00001 percent by weight based on the total weight of the composition.

* * * * *

UNITED STATES PATENT AND TRADEMARK OFFICE
CERTIFICATE OF CORRECTION

PATENT NO. : 9,980,894 B2  
APPLICATION NO. : 14/408117  
DATED : May 29, 2018  
INVENTOR(S) : Herrmann et al.

Page 1 of 1

It is certified that error appears in the above-identified patent and that said Letters Patent is hereby corrected as shown below:

On the Title Page

Item (75), Line 2, inventor "Gerhardd Schmaus" should read --Gerhard Schmaus--

Signed and Sealed this  
Tenth Day of July, 2018

Andrei Iancu  
*Director of the United States Patent and Trademark Office*